United States Patent [19]
Gaiser et al.

[11] Patent Number: 5,712,482
[45] Date of Patent: Jan. 27, 1998

[54] PORTABLE ELECTRONIC RADIOGRAPHIC IMAGING APPARATUS

[75] Inventors: James E. Gaiser, Charlotte; William J. Root, Huntersville; Charles W. Kinsey, Charlotte, all of N.C.

[73] Assignee: Physics Technology, Inc., Huntersville, N.C.

[21] Appl. No.: 691,019

[22] Filed: Aug. 5, 1996

[51] Int. Cl.$^6$ .............................. G03B 42/02; G01T 1/20
[52] U.S. Cl. ................. 250/363.08; 250/368; 378/189; 378/190
[58] Field of Search .................... 250/363.08, 370.09, 250/367, 368; 378/189, 190

[56] References Cited

U.S. PATENT DOCUMENTS

| | | | |
|---|---|---|---|
| 3,434,684 | 3/1969 | Warden | 378/190 X |
| 4,233,516 | 11/1980 | Trepte | 378/189 X |
| 4,365,344 | 12/1982 | Dornheim | 378/189 |
| 4,467,351 | 8/1984 | Wang | |
| 4,890,313 | 12/1989 | Lam et al. | 378/189 |
| 5,034,615 | 7/1991 | Rios et al. | 250/458.1 X |
| 5,198,669 | 3/1993 | Namiki et al. | |
| 5,209,232 | 5/1993 | Levene | |
| 5,231,572 | 7/1993 | Shigyo et al. | |
| 5,231,653 | 7/1993 | Pfeiler et al. | 378/91 |
| 5,278,754 | 1/1994 | Arakawa | |
| 5,514,873 | 5/1996 | Schulze-Ganzlin et al. | 250/370.09 X |

FOREIGN PATENT DOCUMENTS 856797  12/1960  United Kingdom ................... 378/189

OTHER PUBLICATIONS

Brochure entitled "Theraview: Real-Time Radiation Therapy Digital Imaging System, Real Solutions in Real Time", Infimed, Inc., Liverpool, New York, 8 pages (No Date).

Peter Munro, "Portal Imaging Technology: Past, Present, and Future", Seminars in Radiation Oncology, vol. 5, No. 2 (Apr. 1995), pp. 115–133.

Abstract of "Scientific Session X, Electronic Portal Imaging", Wednesday, Oct. 11, 1995, Radiation Oncology, Biology, Physics, vol. 32, Supplement 1.

Dage–MTI, Inc. brochure "MTI 68 Series: Intensified Cameras SIT–68 & ISIT–68", 4 pages (No Date).

Dage–MTI, Inc. brochure "VE–1000 SIT Low Light Level Imaging System", 2 pages, 1993.

Primary Examiner—Edward J. Glick
Attorney, Agent, or Firm—Shefte, Pinckney & Sawyer, LLP

[57] ABSTRACT

Radiographic images may be produced electronically for diagnostic purposes during radiation therapy by utilizing a portable cart-based electronic portal imaging system wherein a photo-stimulable phosphor screen is mounted on the cart by a manipulable stanchion/arm assembly enabling selective positioning movement of the screen horizontally, vertically, and angularly relative to the cart among various spacial orientations as necessary to subtend the radiation beam. A camera and a computer are mounted on the cart to photographically capture and digitize X-ray images produced by the screen and to remotely transmit such images for diagnostic purposes of confirming and, as necessary, adjusting patient positioning.

31 Claims, 5 Drawing Sheets

PORTABLE ELECTRONIC RADIOGRAPHIC IMAGING APPARATUS

FIELD OF THE INVENTION

The present invention relates generally to radiographic imaging apparatus and methodologies and, more particularly, to apparatus and methods for electronically producing radiographic images during radiation therapy and like medical procedures.

BACKGROUND OF THE INVENTION

As is well-known, radiation therapy is a common technique utilized for treating many forms of cancer. Because the dosage levels typically utilized in radiation therapy can be damaging to normal tissue, it is considered to be critical that a prescribed radiation dose be targeted accurately to only the cancerous tumor under treatment. Such radiation therapy is conventionally administered by means of an X-ray generating machine commonly referred to as an "accelerator" having a high energy X-ray source mounted by means of a supporting gantry for rotational positioning through a full 360° range of motion to enable selective geometric orientation of the X-ray beam, commonly referred to as the "port", relative to the tumorous area of the patient's body to be treated, referred to as the "field" so as to best achieve optimal irradiation of the tumor with minimal impact on surrounding tissue, bones, and joints.

Preliminary to prescribing and initiating a course of radiation therapy, a comprehensive series of conventional X-rays of the treatment field of the patient are taken by means of an X-ray machine known as a "simulator" of substantially identical construction to the accelerator, with the capability of executing substantially the identical geometric movements relative to the patient, except that the simulator utilizes a substantially lower dosage of radiation suitable merely for generating conventional X-ray film images. By means of the film images taken of a patient utilizing the simulator, a treating physician is enabled to precisely prescribe the parameters of a specific program of radiation treatment, including particularly the optimal geometric orientation of the port of the accelerator to the patient's body and the precise definition of the field of the patient's body to be irradiated. Depending upon the area of the body, the nature and size of the cancer, and other factors, the actual field to be irradiated will often be irregular, requiring radiation therapists and technicians to use appropriately shaped and positioned lead blocks or plates to shield the adjacent body areas, thereby to define the actual unshielded area to be exposed to the radiation beam ported by the accelerator.

Radiation therapy of the above-described type is most typically administered in periodic doses of radiation over a relatively extended period of time. Studies have shown that discrepancies in the geometric accuracy of radiation treatments can occur frequently and can also negatively affect the treatment results. Hence, it is common practice to take an X-ray image of radiation patients while positioned with respect to the accelerator in order to enable the physician and radiation therapist to ensure that the field of treatment has been correctly defined and does not encompass normal tissue and body areas which are intended to be shielded.

Such diagnostic images may be obtained by two basic types of imaging techniques. First, after positioning the patient with respect to the accelerator, a conventional form of X-ray film cartridge may be positioned opposite the patient from the X-ray source of the accelerator to subtend the beam from the accelerator port. For this purpose, the film cartridge is typically supported by a mobile cart having multiple adjustments so that the film can be positioned to precisely subtend the radiation beam. While this technique has been in common and widespread use for some time, it suffers a number of problems. First, because the lowest level of radiation conventional accelerators are capable of generating is much higher than the radiation levels utilized on traditional X-ray machines such as the aforementioned simulator, the clarity and contrast of the image produced, particularly with respect to the distinction between bone and soft tissue, is poor, making interpretation of the image more difficult. Furthermore, the time required to develop the X-ray film necessarily delays the diagnostic evaluation of the film images and any necessary adjustments in the radiation treatment.

More recently, electronic imaging systems, sometimes referred to as electronic portal imaging devices (EPIDs), have become available. Such imaging systems are mounted directly to the frame of the accelerator to rotate integrally with, but in spaced facing relation to, the X-ray source to be opposite the patient during treatment. These imaging systems utilize a phosphorescent screen subtending the radiation beam so as to create a luminescent image of the patient's body field and the shielding utilized in the therapy. Such image is captured by a camera directed by a reflective mirror at the screen and the photographic image is digitized for viewing on a computer monitor and for digital storage in the computer memory and, as desired, downloading to a storage disk. Unfortunately, conventional electronic imaging systems of this type suffer their own disadvantages. First, since such systems are mounted directly to the frame of the accelerator, they are generally viewed as less convenient than utilizing a cart-supported film imaging system. It is also not uncommon for such systems to require a higher dose of radiation than is necessary with film-tube imaging and the resultant image therefore does not provide any significantly better contrast and clarity than a film image.

SUMMARY OF THE INVENTION

It is accordingly a basic object of the present invention to provide an improved electronic portal imaging system which overcomes the foregoing disadvantages of conventional systems. A more specific object of the present invention is to provide a portable electronic imaging system which does not require mounting to the accelerator. A further object of the present invention is to provide a complete self-contained electronic portal imaging device compactly mounted on a rollable or otherwise movable cart structure for easy portability and with a variably positionable phosphorescent screen as an X-ray detector enabling orientation of the screen to subtend the accelerator's port in substantially any portal disposition of the accelerator. Other objects of the invention will be apparent from the description which follows.

Briefly summarized, the radiographic imaging apparatus of the present invention basically comprises a movable support structure which is transportable to and from, and selectively positionable relative to, a radiation source such as the port of a conventional accelerator used in radiation therapy. An imaging screen comprising a photo-stimulable phosphor-containing composition is mounted on the support structure for selective positioning movement of the screen among various spacial orientations relative to the support structure so as to be manipulable to subtend any of variously directed radiation beams. The support structure additionally has mounted thereto appropriate means for capturing in digital form images produced by the screen.

Various embodiments of the basic portable apparatus of the present invention will be recognized to be possible. In a preferred embodiment, adapted particularly for use during radiation therapy, the support structure is a wheeled cart on which is fixed an upstanding stanchion with an arm extending outwardly from the stanchion to support the imaging screen for selective positioning movement horizontally, vertically, and angularly relative to the cart. In particular, the arm is movable vertically along and horizontally and rotatably with respect to the stanchion, with a housing mounted pivotably at an outward end of the arm for supporting the imaging screen in an exposed disposition. In this manner, adjusting movements of the arm and housing enable the selective positioning of the screen with respect to the radiation source of an accelerator so as to subtend the radiation beam opposite the patient's body from the radiation source in substantially any portal direction of the radiation beam.

An imaging surface of the screen faces interiorly within the housing and a camera (or an equivalent device) is mounted to the housing to face a mirror disposed within the housing interior for reflecting the imaging surface of the screen to the camera for purposes of photographing or otherwise recording or capturing the images produced by the screen in a form which is in, or can be converted into, human viewable form. A computer or other digital processor is mounted on the cart and connected to the camera for storing the photographed images in digital form. Depending upon the particular type of camera utilized, the image output signal produced by the camera may be in analog or digital form. If the camera output signal is an analog signal, the computer may include software or may have an internal or external device for converting the analog signal into digital form. The computer may also include a monitor or other display screen also mounted on the cart.

The computer or processor also preferably has an associated infrared or other wireless transmitting device by which the digital form images may be transmitted to a remote computer, e.g., at an operator station for the accelerator, at which the digital form images may be viewed and stored. A battery or other form of self-contained electric power source is mounted on the cart to supply operating electric current to the camera, the computer and any other of the electronic devices on the cart requiring an independent power source.

DESCRIPTION OF THE PREFERRED EMBODIMENT

Figure 1:
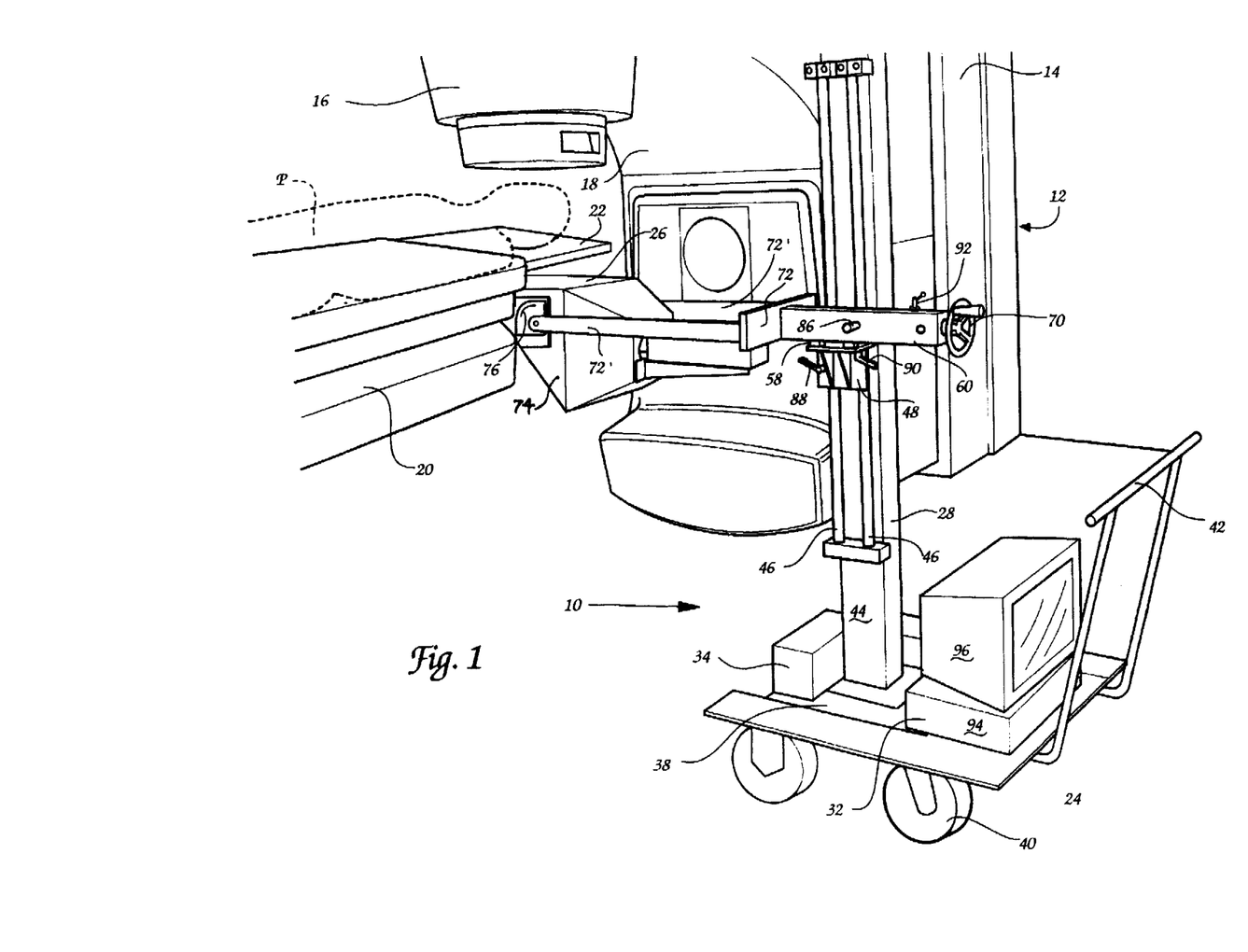
FIG. 1 is a perspective view of a preferred embodiment of the portable electronic radiographic imaging apparatus of the present invention, shown in use in association with a conventional form of X-ray accelerator utilized in radiation therapy.

Referring now to the accompanying drawings and initially to FIG. 1, a cart-mounted portable imaging apparatus in accordance with a preferred embodiment of the present invention, is shown generally at 10, positioned in operative relationship to a conventional form of X-ray accelerator 12 for use to generate diagnostic images during radiation treatment of a patient P.

The basic construction and operation of the accelerator 12 is well-known and does not form a part of the present invention. Basically, the accelerator comprises a fixed floor-standing gantry or frame 14 on which an X-ray beam generator 16 is mounted in cantilevered fashion on a sub-frame 18 rotatably supported on the gantry 14 for movement about a horizontal axis through a full 360° range of movement. A table 20 is positioned adjacent the accelerator 12 and is equipped with a horizontally slidable platform 22 forming an upper support surface for the patient P. Depending upon the nature and location of the cancerous tumor of the patient P to be treated, the patient P is placed in a predetermined position on the table platform 22 and the subframe 18 of the accelerator 12 is rotated to position the X-ray generator 16 in a compatible orientation to direct an X-ray beam through the cancerous field of the patient's body to apply an optimal dose of radiation to the tumor. As previously mentioned, appropriate lead blocks, plates, etc. (not shown) may be placed on the patient to shield the surrounding tissue and bone from the radiation.

The portable cart-mounted apparatus 10 is adapted to permit a phosphorescent image of the affected area of the patient's body to be generated during such therapy utilizing the accelerator's X-ray generator 16 to supply the necessary radiation, thereby to permit diagnostic evaluation of the geometric accuracy of the radiation therapy, i.e., to ensure consistency with the prescribed course of treatment.

Basically, the imaging apparatus 10 of the present invention includes a rollable cart 24 on which a photo-stimulable imaging screen 26 is supported for variable positionability by a stanchion/arm assembly, indicated generally at 28. A camera 30 is also supported on the stanchion/arm assembly 28 in association with the screen 26 for photographically capturing images produced by the screen 26 and a digital processor 32 is operatively connected with the camera 30 to receive and process the photographic images. A battery or other self-contained electric power source, indicated only schematically at 34, provides operating electrical current to the camera 30 and the processor 32.

The cart 24 has a generally horizontal base 38 at it lower end mounted on a plurality of wheels 40 for floor support of the apparatus 10 for rolling movement into and out of operative disposition relative to the accelerator 12. An upwardly extend handle 42 is affixed to the base 38 to facilitate ease of manual rolling movement of the cart 24.

Figure 2:
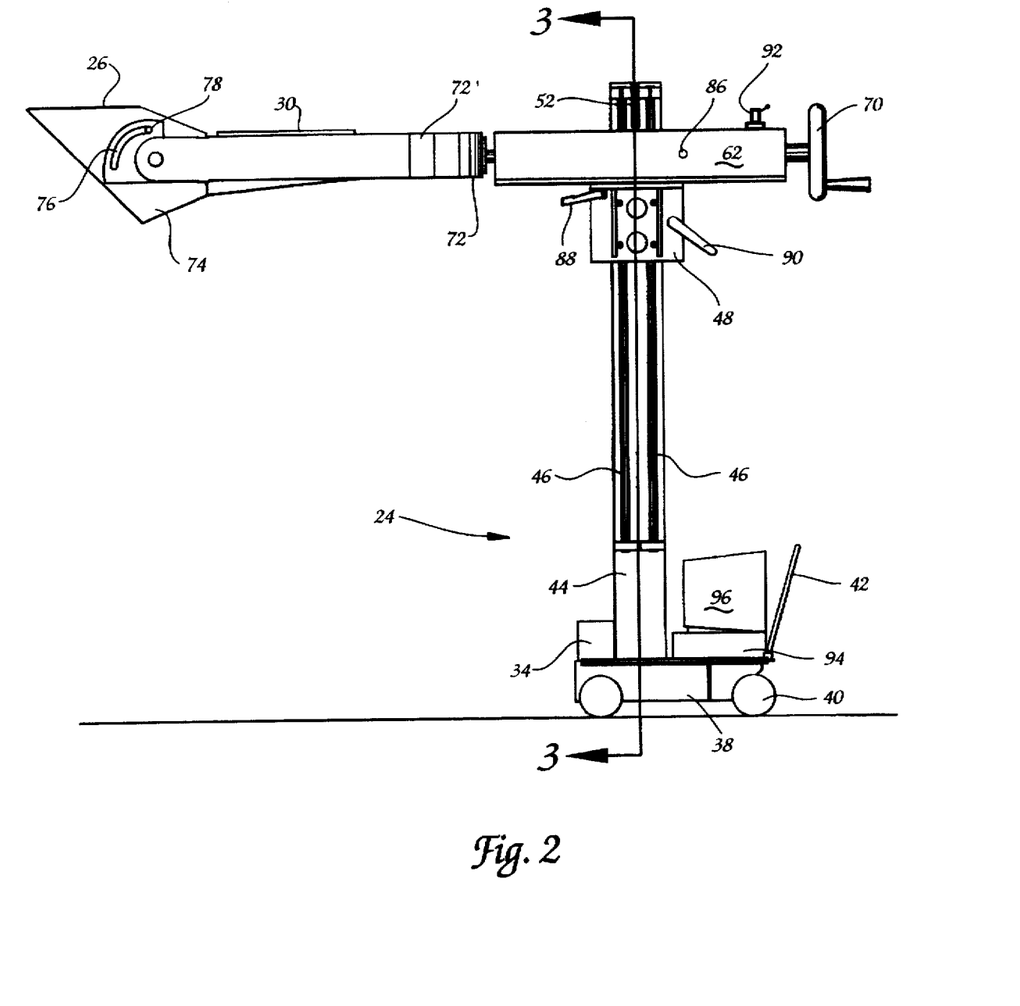
FIG. 2 is a front elevational view of the imaging apparatus of FIG. 1.
Figure 3:
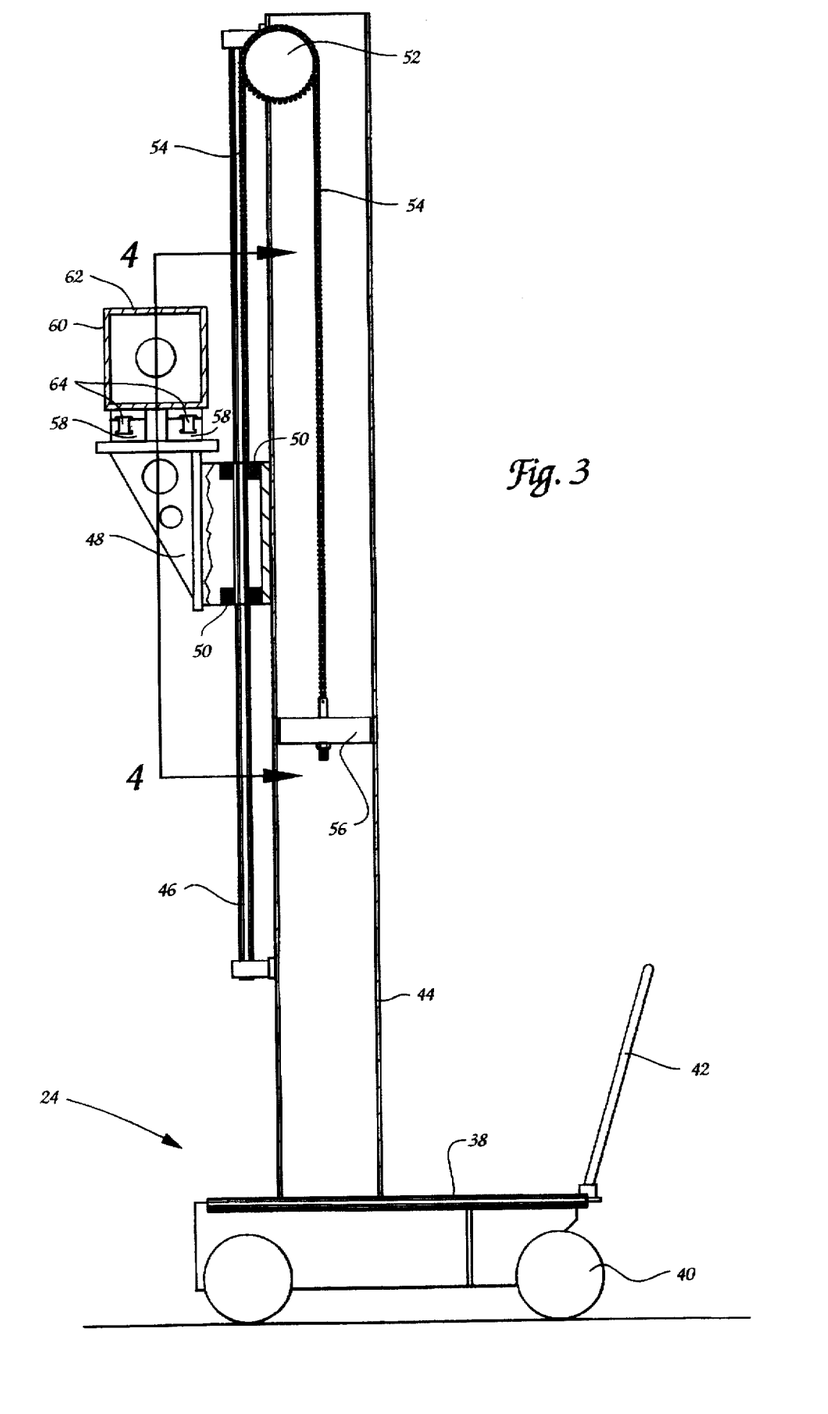
FIG. 3 is a vertical cross-sectional view of the portable imaging apparatus of FIGS. 1 and 2, taken along line 3—3 of FIG. 2.
Figure 4:
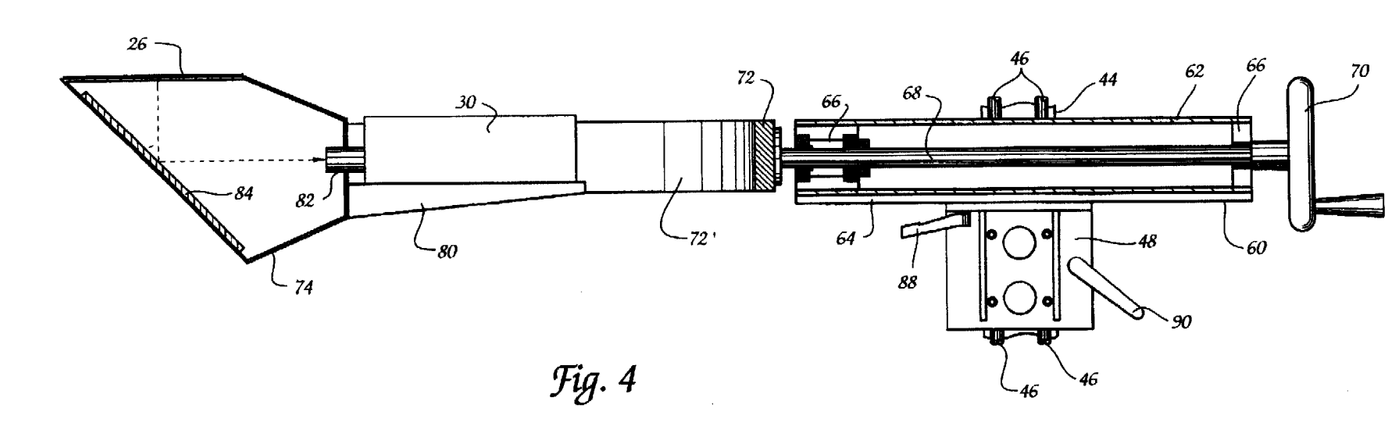
FIG. 4 is a horizontal cross-sectional view of the portable imaging apparatus of FIGS. 1 and 2, taken along line 4—4 of FIG. 3.

With reference to FIGS. 2–4, the stanchion/arm assembly 28 is mounted on the base 38 of the cart 24 and includes an upright stanchion 44 rigidly fixed at its lower end centrally to the base 38 and extending vertically therefrom. The stanchion 44 is of a hollow substantially square cross-section, with a pair of guide rods 36 fixed outwardly to one side of the stanchion 44 and extending vertically in parallel spaced relation along the predominate vertical extent of the stanchion 44. A slide block 48 is mounted on the guide rods 46 by a corresponding pair of spaced bearings 50 extending vertically through the slide block 48 for sliding vertical movement thereof along the guide rods 46. A sprocket wheel 52 is rotatably supported at the upper end of the stanchion 44 and a timing chain 54 is trained about the sprocket wheel 52, one end of the timing chain 54 being affixed to the slide block 48 and the opposite end extending into the hollow interior of the stanchion 44 and affixed thereat to a counterweight 56 (FIG. 3).

The slide block 48 has a horizontal upper surface on which four bearing blocks 58 are fixed in spaced rectangular relation to one another. The stanchion/arm assembly 28 further includes a horizontal arm assembly 60 having a main linear arm element 62 with a pair of linear guide rails 64 extending along the underside of the main arm element 62 for its entire length and guided by the bearing blocks 58 for sliding movement of the arm assembly 60 horizontally with respect to the stanchion 44. A pair of bearing sleeves 66 are fixed within the opposite ends of the hollow interior of the main arm element 62 and rotatably support a linear shaft 68. A control wheel 70 is affixed to one end of the shaft 68 outwardly of the corresponding end of the main arm element 62 and a U-shaped yoke 72 is affixed to the opposite end of the shaft 68 outwardly of the corresponding end of the main arm element 62 opposite the control wheel 70.

A screen housing 74 is pivotably supported between the opposed arms 72' of the yoke 72 for a limited 90° range of pivoting movement defined by an arcuate slot 76 formed in one yoke arm 72', through which a securing pin 78 on the screen housing 74 extends.

The screen 26 is affixed to one face of the housing 74 and basically comprises a planar plate formed of copper or another suitable metal with its underside facing interiorly within the housing 74 being coated with a phosphor composition or another suitable photo-stimulable composition adapted to luminesce when exposed to X-ray radiation in relation to the amount of such radiation. Extending from the opposite side of the screen housing 74 is a support arm 80 on which the camera 30 is mounted with its lens 82 extending through an adjacent opening in the housing 74 along a line of sight essentially perpendicular to the plane of the screen 26. A reflecting mirror 84 (FIG. 4) is disposed within the screen housing 74 at substantially a 45° angle to reflect electro-luminescent images produced by the coating composition on the underside of the screen 26 into the lens of the camera 30.

The camera 30 is preferably a video camera having a high level of optical sensitivity in low light conditions. Various types of conventional cameras are deemed to be suitable for this purpose; for example, a conventional form of SIT (silicon intensified target) camera such as the NTI 68 series SIT-68 or ISIT-68 cameras produced by Dage MTI, Inc. of Michigan City, Ind., or alternatively, a camera of the CID (charge injection device) type, such as manufactured by CID Technologies, Inc. of Syracuse, N.Y. As will be understood, an SIT camera produces an analog video output signal, whereas a CID camera produces a digital video output signal, as will be discussed more fully hereinafter.

The basic mechanical operation of the cart 24 will thus be understood. Once a patient P undergoing radiation therapy has been positioned on the platform 22 of the table 20, the subframe 18 of the accelerator 12 has been rotatably positioned relative to the patient P and appropriate lead blocks or other shields have been placed on the patient according to the prescribed course of treatment, an X-ray image of the thusly-defined field of the patient's body can be produced utilizing the cart 24. Initially, the cart 24 is rolled to a convenient position adjacent the table 20. Depending upon the disposition of the patient and the disposition of the accelerator subframe 18, the arm assembly 60 is raised or lowered manually along the vertical guide rods 46 on the stanchion 44. A handle 86 extends outwardly from the main arm element 62 to assist in such manual movement. By virtue of the counterweight 56 attached to the timing chain 54, only minimal manual effort is required to initiate and sustain such manual movement of the arm assembly 60. Once positioned, the vertical disposition of the arm assembly 60 may be fixed by means of a tightening bolt 88 extending through the slide block 48. The handle 86 also facilitates horizontal movement of the arm assembly 60 laterally with respect to the stanchion 28 under the guided constraint of the rail 64 by the bearing blocks 58. Once a desired horizontal disposition of the arm assembly 60 is reached, another tightening bolt 90 on the slide block 48 enables the position of the arm assembly to be fixed. The control wheel 70 allows the yoke 72 and the screen housing 74 to be rotated selectively through a 360° range of motion and a tightening bolt 92 on the main arm element 62 enables a desired rotational position of the yoke 72 and the screen housing 74 to be fixed. Additionally, by means of the securing pin 78, the pivoted disposition of the screen housing 74 relative to the yoke 72 may be adjusted and fixed.

Through these differing adjustments, the plane of the screen 26 can be selectively positioned opposite the patient P from the X-ray generator 16 to subtend the X-ray beam in precise perpendicular relation thereto. Upon energizing the X-ray generator 16, typically only at its lowest energy level, free electrons in the copper sheet are liberated under the influence of the X-ray beam and cause the phosphor coating on the underside of the plate to luminesce in relation to the amount of X-ray energy. As will be understood, the phosphor screen is variably luminesced according to the radiation absorbed or blocked by the lead shielding on the patient, the patient's bone structure, and the patient's soft tissue, thereby producing a corresponding luminescent image, which is photographically captured by the camera 30.

Figure 5:
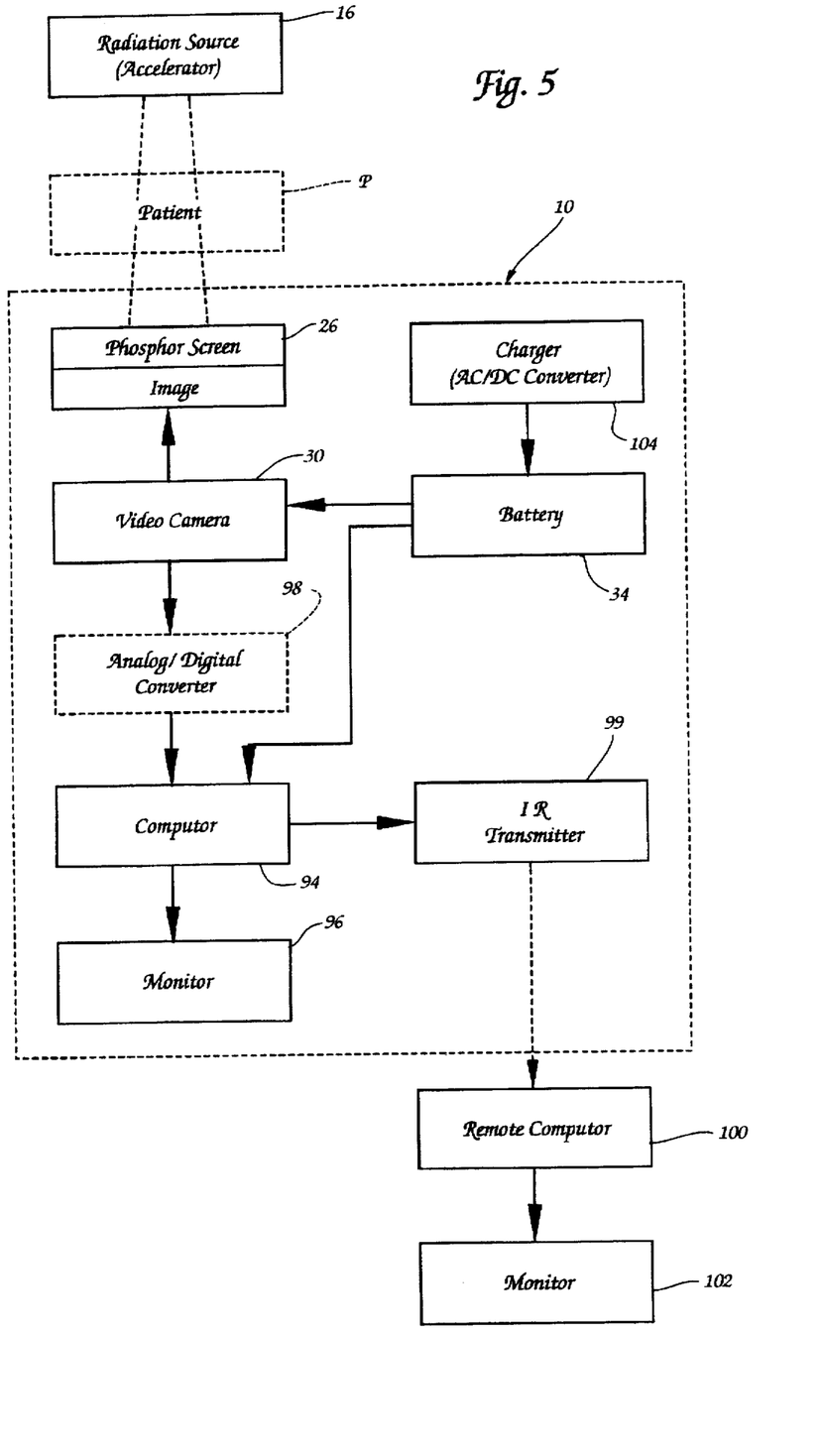
FIG. 5 is a schematic block diagram depicting the functional relationship between the various operating components of the portable imaging apparatus of FIGS. 1 and 2.

As schematically represented in FIG. 5, the processor 32 serves to store, display, and transmit in digital form the photographed image from the screen 26. In the preferred embodiment, the processor 32 will preferably be a conventional form of PC computer, indicated schematically at 94, with an associated video monitor or other form of display screen 96, preferably mounted as a unit on the base 38 of the cart 24, whereby through appropriate software (which does not form a part of the present invention), image output signals received from the video camera 30 may be stored in digital form in memory and, as necessary or desirable, downloaded onto a magnetic disk or other storage medium, as well as visually inspected on the monitor 96.

In the event the camera 30 is of the SIT type, the analog video output signal produced by the camera must be digitized initially, which can be accomplished by means of appropriate program control software stored in the computer 94 or by connecting an analog-to-digital convertor 98 between the camera 30 and the computer 94.

While it is advantageous and desirable for the computer 94 mounted on the cart 24 to have the full capability of storing, displaying, and downloading digital images, it will be understood that the technician or other operator of the accelerator 12 is required for safety reasons to leave the vicinity of the accelerator 12 when the X-ray generator 16 is energized and operated. Standard procedures typically dictate that the room in which the accelerator 12 is operated be shielded from the surrounding areas of the same building and the controls for the accelerator 12 are therefore positioned outside the room for remote operation by the technician. Hence, it is equally, if not more desirable, for the computer 94 or other processor to have the capability of remotely transmitting the digital images created from the camera signals to another computer or other remote storage and display means at which the technician can view the images without reentering the treatment room. For this purpose, the present imaging apparatus 10 is additionally equipped with an infrared transmitter 99 connected to the computer 94 as a peripheral device, by which the computer 94 can transmit the digital images wirelessly to a remote computer 100, preferably at the operator's station, for viewing on an associated monitor or display screen 102.

The battery 34 may be of substantially any conventional type compatible with the computer 94 and the camera 30. Preferably, a charging device 104 is associated with the battery 34 to permit periodic recharging of the battery after periods of use. For example, a conventional lead/acid battery may be utilized in conjunction with a sine wave inverter-type charger, which also provides the capability of serving as an AC/DC convertor so that, if necessary, the apparatus 10 can be operated from a standard AC power supply outlet or another appropriate DC power supply as may be necessary or desirable.

The advantages of the present portable imaging apparatus will be readily understood. In contrast to conventional EPIDs (electronic portal imaging devices), the present apparatus is completely detached from the accelerator and totally portable, thereby providing greater flexibility and convenience in use and posing no impediment to the normal operation of the accelerator 12.

In contrast to conventional film-type imaging systems, the electronic images can be produced and evaluated immediately in "real time", eliminating the necessity and attendant delay in development of the film images. By utilizing a so-called "fast" phosphorescent screen, i.e., having a phosphorescent coating adapted to maximize the output of luminescent light in relation to the amount of radiation energy received by the screen, the amount of radiation needed to produce an image of satisfactory contrast and clarity can be substantially reduced in relation to that conventionally necessary with accelerator-mounted EPIDs to a radiation level comparable to that utilized for developing film-based images.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. An apparatus for electronic generation of radiographic images during medical procedures, the apparatus comprising:

a movable support structure transportable to and from, and selectively positionable relative to, a radiation source;

an imaging screen comprising a photostimulable composition;

means mounting the screen on the support structure for selective positioning movement of the screen among various spatial orientations thereof relative to the radiation source; and means mounted on the support structure for capturing in electronic form images produced by the screen;

wherein the means mounting the screen on the support structure comprises an upstanding stanchion fixed on the support structure, an arm extending laterally outwardly from the stanchion and defining a longitudinal arm axis, means for moving the arm vertically along the stanchion and rotatably with respect to the longitudinal arm axis, and means mounting the screen pivotably with respect to the arm.

2. An apparatus for electronic generation of radiographic images during medical procedures according to claim 1, wherein the movable support structure comprises a wheeled cart.

3. An apparatus for electronic generation of radiographic images during medical procedures according to claim 1, wherein the means for moving the arm comprises means for moving the arm horizontally with respect to the stanchion.

4. An apparatus for electronic generation of radiographic images during medical procedures according to claim 1, wherein the means mounting the screen on the support structure comprises a housing supporting the screen in an exposed disposition with an imaging surface of the screen facing interiorly within the housing and wherein the means for capturing images comprises a camera mounted to the housing to face interiorly therewithin.

5. An apparatus for electronic generation of radiographic images during medical procedures according to claim 4, wherein the housing comprises means for reflecting the imaging surface of the screen to the camera.

6. An apparatus for electronic generation of radiographic images during medical procedures according to claim 4, wherein the means for capturing images comprises digital processing means operatively connected to the camera to receive an image output signal therefrom.

7. An apparatus for electronic generation of radiographic images during medical procedures according to claim 6, wherein the camera is adapted to produce the image output signal in analog form and the digital processing means further comprises means for converting the analog image output signal into digital form.

8. An apparatus for electronic generation of radiographic images during medical procedures according to claim 6, wherein the digital processing means comprises a computer with an associated display monitor.

9. An apparatus for electronic generation of radiographic images during medical procedures according to claim 8, and further comprising an electrical power source mounted on the support structure and connected to the camera and the digital processing means for supplying operating electrical current thereto.

10. An apparatus for electronic generation of radiographic images during medical procedures according to claim 6, wherein the digital processing means includes memory means for storing in digital form images received from the camera.

11. An apparatus for electronic generation of radiographic images during medical procedures according to claim 6, wherein the digital processing means comprises means for wirelessly transmitting digital form images received from the camera to a remote digital display device.

12. An apparatus for electronic generation of radiographic images during medical procedures according to claim 1, wherein the screen comprises a phosphorescent photostimulable composition.

13. An apparatus for electronic generation of radiographic images during medical procedures wherein a radiation source may be selectively oriented to direct a radiation beam in diverse portal directions to deliver a radiation dose to a predetermined field of a patient's body to be treated, the apparatus comprising:

a wheeled cart transportable to and from, and selectively positionable relative to, the radiation source;

an imaging screen comprising a photostimulable composition;

means mounting the screen on the cart for selective positioning movement of the screen relative to the cart among various spatial orientations of the screen with respect to the radiation source so as to subtend the radiation beam opposite the patient's body from the radiation source in substantially any portal direction of the radiation beam;

means mounted on the cart for capturing in electronic from images produced by the screen;

processing means communicating with the image capturing means for receiving and displaying the captured images;

wherein the means mounting the screen on the cart comprises an upstanding stanchion fixed on the cart, an arm extending laterally outwardly from the stanchion and defining a longitudinal arm axis, means for moving the arm vertically along the stanchion and rotatably with respect to the longitudinal arm axis, and means mounting the screen pivotably with respect to the arm.

14. An apparatus for electronic generation of radiographic images during medical procedures according to claim 13, wherein the means for moving the arm comprises means for moving the arm horizontally with respect to the stanchion.

15. An apparatus for electronic generation of radiographic images during medical procedures according to claim 13, wherein the means mounting the screen on the cart comprises a housing supporting the screen in an exposed disposition with an imaging surface of the screen facing interiorly within the housing, the means for capturing images comprises a camera mounted to the housing to face interiorly therewithin, and the housing comprises means for reflecting the imaging surface of the screen to the camera.

16. An apparatus for electronic generation of radiographic images during medical procedures according to claim 15, and further comprising an electrical power source mounted on the cart end connected to the camera for supplying operating electrical current thereto.

17. An apparatus for electronic generation of radiographic images during medical procedures according to claim 13, wherein the processing means comprises a computer with an associated display monitor.

18. An apparatus for electronic generation of radiographic images during medical procedures according to claim 13, wherein the processing means includes memory means for storing in digital from images received from the camera.

19. An apparatus for electronic generation of radiographic images during medical procedures according to claim 13, wherein the screen comprises a phosphorescent photostimulable composition.

20. An apparatus for electronic generation of radiographic images during medical procedures according to claim 13, and further comprising means for wirelessly transmitting the electronic form images from the image capturing means to the processing means.

21. An apparatus for electronic generation of radiographic images during radiation therapy procedures wherein a radiation source may be selectively oriented to direct a radiation beam in diverse portal directions to deliver a radiation dose to a predetermined field of a patient's body to be treated, the apparatus comprising:

a wheeled cart transportable to and from, and selectively positionable relative to, the radiation source;

an imaging screen comprising a photostimulable composition;

means mounting the screen on the cart for selective positioning movement of the screen relative to the cart among various spatial orientations of the screen with respect to the radiation source so as to subtend the radiation beam opposite the patient's body from the radiation source in substantially any portal direction of the radiation beam, the means mounting the screen on the cart comprising an upstanding stanchion fixed on the cart, an arm extending laterally outwardly from the stanchion and defining a longitudinal arm axis, means for moving the arm vertically along the stanchion and rotatably with respect to the longitudinal arm axis, and a housing mounted pivotably with respect to the arm, the housing supporting the screen in an exposed disposition with an imaging surface of the screen facing interiorly within the housing;

camera means mounted to the housing to face interiorly thereof and a mirror within the housing for reflecting the imaging surface of the screen to the camera means for capturing images produced by the screen; and computer means communicating with the camera means for storing and displaying the photographed images in digital form.

22. An apparatus for electronic generation of radiographic images during medical procedures according to claim 21, wherein the screen comprises a phosphorescent photostimulable composition.

23. An apparatus for electronic generation of radiographic images during medical procedures, the apparatus comprising:

a rollable support structure transportable to and from, and selectively positionable relative to, a radiation source;

an imaging device for detecting the radiation source and producing a corresponding electronic image; and an arm arrangement mounted on the support structure and defining a longitudinal arm axis, the arm arrangement supporting the imaging device for selective movement vertically relative to the support structure and rotatably relative to the arm axis for selective positioning movement of the imaging device among various spatial orientations thereof relative to the radiation source, and wherein the imaging device is pivotable with respect to the arm arrangement.

24. An apparatus for electronic generation of radiographic images during medical procedures according to claim 23, wherein the imaging device comprises an imaging screen with an imaging surface, and wherein the arrangement supporting the imaging device on the support structure comprises a housing supporting the screen in an exposed disposition with the imaging surface of the screen facing interiorly within the housing and wherein means for capturing in electronic form images produced by the screen is mounted to the housing to face interiorly therewithin.

25. An apparatus for electronic generation of radiographic images during medical procedures according to claim 24, wherein the means for capturing images comprises a camera and the housing comprises means for reflecting the imaging surface of the screen to the camera.

26. An apparatus for electronic generation of radiographic images during medical procedures according to claim 24, and further comprising means for transmitting the electronic form images to a display monitor for viewing.

27. An apparatus for electronic generation of radiographic images during medical procedures wherein a radiation source may be selectively oriented to direct a radiation beam in diverse portal directions to deliver a radiation dose to a predetermined field of a patient's body to be treated, the apparatus comprising:

a wheeled cart transportable to and from, and selectively positionable relative to, the radiation source;

an imaging screen comprising a photostimulable composition;

an arm arrangement mounted on the cart and defining a longitudinal arm axis, the arm arrangement supporting the imaging screen for selective movement vertically relative to the cart and rotatably relative to the arm axle for selective positioning movement of the screen among various spatial orientations thereof with respect to the radiation source so as to subtend the radiation beam opposite the patient's body from the radiation source in substantially any portal direction of the radiation beam and wherein the imaging screen is pivotable with respect to the arm arrangement;

means mounted on the cart for capturing in electronic form images produced by the screen; and processing means communicating with the image capturing means for receiving and displaying the captured images.

28. An apparatus for electronic generation of radiographic images during medical procedures according to claim 27, wherein the imagine screen has an imaging surface, and wherein the arrangement supporting the imaging screen on the cart comprises a housing supporting the screen in an exposed disposition with the imaging surface of the screen facing interiorly within the housing and wherein means for capturing in electronic form images produced by the screen is mounted to the housing to face interiorly therewithin.

29. An apparatus for electronic generation of radiographic images during medical procedures according to claim 28, wherein the means for capturing images comprises a camera and the housing comprises means for reflecting the imaging surface of the screen to the camera.

30. An apparatus for electronic generation of radiographic image during medical procedures according to claim 28, and wherein the processing means comprises means for transmitting the electronic form images to a display monitor for viewing.

31. An apparatus for electronic generation of radiographic images during medical procedures according to claim 30, wherein the processing means comprises a computer.

* * * * *

UNITED STATES PATENT AND TRADEMARK OFFICE
CERTIFICATE OF CORRECTION

PATENT NO. : 5,712,482
DATED : January 27, 1998
INVENTOR(S): Gaiser et al.

It is certified that error appears in the above-identified patent and that said Letters Patent is hereby corrected as shown below:

Col. 4, line 46, delete "it" and insert --its--
Col. 4, line 50, delete "extend" and insert --extending--
Col. 4, line 59, delete "predominate" and insert --predominately--
Col. 9, line 24, delete "from" and insert --form--
Col. 9, line 51, delete "end" and insert --and--
Col. 11, line 21, delete "axle", and insert --axis--
Col. 12, line 8, delete "imagine" and insert --imaging--
Col. 12, line 20, delete "image" and insert --images--

Signed and Sealed this

Eighteenth Day of May, 1999

Attest:

Attesting Officer

Q. TODD DICKINSON

Acting Commissioner of Patents and Trademarks